United States Patent [19]

Ross et al.

[11] 4,438,116

[45] Mar. 20, 1984

[54] QUINOXALINYLOXY-AMINO-PROPANOL COMPOUNDS WITH BLOOD PRESSURE LOWERING AND β-BLOCKING PROPERTIES, THEIR USE AND PHARMACEUTICAL COMPOSITIONS CONTAINING THEM

[75] Inventors: Carl H. Ross, Viernheim; Wolfgang Kampe, Heddesheim; Wolfgang Bartsch, Viernheim; Gisbert Sponer, Hemsbach; Egon Roesch, Mannheim, all of Fed. Rep. of Germany

[73] Assignee: Boehringer Mannheim GmbH, Mannheim, Fed. Rep. of Germany

[21] Appl. No.: 302,894

[22] Filed: Sep. 16, 1981

Related U.S. Application Data

[63] Continuation of Ser. No. 153,308, May 27, 1980, abandoned.

[30] Foreign Application Priority Data

May 31, 1979 [DE] Fed. Rep. of Germany ....... 2922084

[51] Int. Cl.³ ................. C07D 241/44; C07D 241/42; A61K 31/495; A61K 31/505
[52] U.S. Cl. .................................... 424/250; 544/295; 544/344
[58] Field of Search ................. 544/295, 354; 424/250

[56]  References Cited
U.S. PATENT DOCUMENTS 4,140,789  2/1979  Jaeggi et al. ........................ 544/354

Primary Examiner—Mark L. Berch
Attorney, Agent, or Firm—Felfe & Lynch

[57] ABSTRACT

An aminopropanol compound of the formula

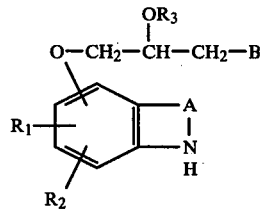

wherein
 $R_1$ and $R_2$ are individually selected from hydrogen and lower alkyl; or
 $R_1$ and $R_2$ together represent an alkylene radical;
 $R_3$ is hydrogen or acyl;
 A is one of the following structures

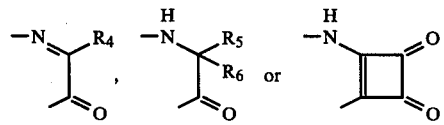

wherein
 $R_4$ is hydrogen or lower alkyl optionally substituted by hydroxyl halogen and lower alkylthio; and
 $R_5$ and $R_6$ are individually selected from lower alkyl;
 B is alkylamino which optionally carries a phenyl and a phenoxy radical optionally substituted by at at least one of halogen, hydroxyl or lower alkyl, lower acyl, lower alkylthio, acylamino, aminocarbonyl, lower alkoxy, lower alkenyloxy, phenoxy, lower alkenyl, lower alkylsulphonyl, lower alkylsulphinyl or haloalkyl; or
 B is an aryl- or heteroaryloxymethylpiperidine radical optionally substituted by at least one of halogen hydroxyl or lower alkyl, hydroxyl alkyl or carboxamido alkyl, or by lower alkoxy, lower acyl, amino, carboxamido, lower alkylcarbonylamido or lower alkylsulphonylamino;

and the pharmacologically acceptable salts thereof, are outstandingly effective beta blockers and blood-pressure depressants.

21 Claims, No Drawings

QUINOXALINYLOXY-AMINO-PROPANOL COMPOUNDS WITH BLOOD PRESSURE LOWERING AND β-BLOCKING PROPERTIES, THEIR USE AND PHARMACEUTICAL COMPOSITIONS CONTAINING THEM

This is a continuation application of Ser. No. 153,308 filed May 27, 1980, now abandoned.

This invention relates to new aminopropanol compounds, to pharmaceutical compositions containing them, and to methods of combating cardiac and circulatory insufficiencies.

The new aminopropanol derivatives according to the present invention are compounds of the formula

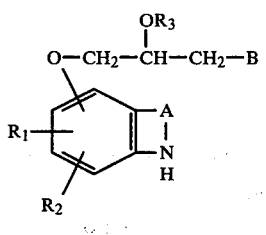

wherein
$R_1$ and $R_2$, which can be the same or different, are hydrogen atoms or lower alkyl radicals or together represent an alkylene radical;
$R_3$ is a hydrogen atom or an acyl radical;
A is one of the following structural elements

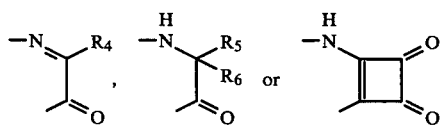

wherein
$R_4$ is a hydrogen atom or lower alkyl radical which is optionally substituted by halogen, hydroxyl, phenyl or alklylthio; and
$R_5$ and $R_6$, which can be the same or different, are lower alkyl radicals, and
B is an alkylamino radical which can carry a phenyl and/or phenoxy radical, which can be substituted one or more times by halogen, hydroxyl, lower alkyl, lower acyl, lower alkylthio, acylamino, aminocarbonyl, lower alkoxy, lower alkenyloxy, phenoxy, lower alkenyl, lower alkylsulphonyl, lower alkylsulphinyl or haloalkyl, or is an aryl- or heteroaryloxymethyl-piperidine radical which can be substituted one or more times by halogen, hydroxyl or lower alkyl, which can bear a hydroxyl or carboxamido substituent, a lower alkoxy, lower acyl, amino, carboxamido, lower alkylcarbonylamido or lower alkylsulphonylamino radical; and the pharmacologically acceptable salts thereof.

Compounds of general formula (I) contain an asymmetric carbon atom and can, therefore, be present in optically-active form or as a racemic mixture. The present invention includes not only the racemic forms but also the optical isomers.

The alkylamino radicals in the definition of B are derived from lower alkylamines containing up to 6 carbon atoms and preferably 2 to 4 carbon atoms, preferred amines including isopropylamine, tert.-butylamine, sec.-butylamine and substituted and unsubstituted phenyl- and phenoxyethylamine and -propylamine.

The acyl radicals which are possibly represented by $R_3$ can be acid residues of straight-chained and branched aliphatic carboxylic acids containing 2 to 6 carbon atoms or of aromatic carboxylic acids optionally substituted by halogen atoms or by lower alkyl or lower alkoxy radicals. Preferred acyl radicals include the acetyl, pivaloyl and benzoyl radicals.

The lower alkyl and alkoxy radicals which occur in the definitions of the substituents $R_1$, $R_2$, $R_3$, $R_4$, $R_5$ and B can be straight-chained or branched and contain up to 6 and preferably up to 4 carbon atoms, preferred radicals of this kind including the methyl, methoxy, ethoxy and propoxy radicals.

The alkylene radical which can be formed by the substituents $R_1$ and $R_2$ together can contain 2 to 4 carbon atoms and is preferably in the ortho position.

The term halogen means, according to the present invention fluorine, chlorine, bromine or iodine, fluorine, chlorine and bromine being preferred.

By an aryl or heteroaryl radical in the definition of substituent B, there is to be understood a carbocyclic or heterocyclic monocyclic or bicyclic radical, for example a phenyl, naphthyl, pyridyl, pyrimidyl or benzimidazolinyl radical, the phenyl, pyridyl and benzimidazolinyl radicals being especially preferred.

The compounds of general formula (I), as well as their pharmacologically acceptable salts, inhibit adrenergic β-receptors and, at the same time, lower the blood pressure to a great extent. Therefore, they are suitable for the treatment and prophylaxis of cardiac and circulatory diseases.

It is known that aminopropanols of similar structure have similar actions. However, by the introduction of the new heterocyclic phenol components, a surprising improvement of the quality of action is achieved.

The new compounds of general formula (I) according to the present invention can be prepared, for example, by one of the following methods:

(a) reaction of a compound of the general formula:

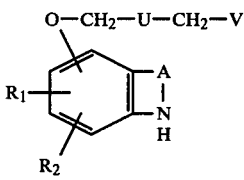

with a compound of the general formula:

H—B    (III), in which $R_1$, $R_2$, A and B have the same meanings as above, V represents a reactive residue and U stands for the group

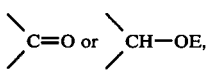

E being a hydrogen atom or an acyl radical or, together with V, forming a single bond, and, if U is the group

subsequent reduction of the product obtained; or
(b) reaction of a compound of the general formula:

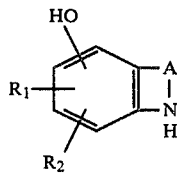 (IV)

with a compound of the general formula:

V—CH$_2$—U—CH$_2$—B          (V), in which R$_1$, R$_2$, A, B, U and V have the same meanings as above, and, if U is the group

subsequent reduction of the product obtained; or
(c) when A stands for the grouping

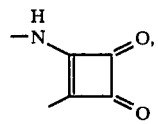

reaction of a compound of the general formula:

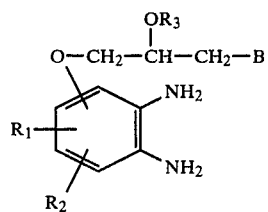 (VI)

with a compound of the general formula:

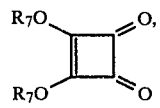 (VII)

in which R$_1$, R$_2$, R$_3$ and B have the same meanings as above and R$_7$ is a hydrogen atom or a lower alkyl radical; or
(d) when A stands for the grouping

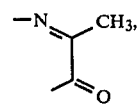

reaction of a compound of general formula (VI) with acetylenedicarboxylic acid; or
(e) when A stands for the grouping

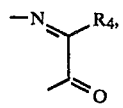

reaction of a compound of the general formula (VI) with a compound of the general formula:

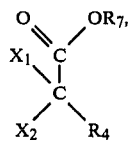 (VIII)

in which R$_4$ and R$_7$ have the same meanings as above, X$_1$ is a halogen atom and X$_2$ is a hydrogen atom or X$_1$ and X$_2$ together represent an oxygen atom, and, when X$_2$ is a hydrogen atom, subsequent oxidation; or
(f) when A stands for the grouping

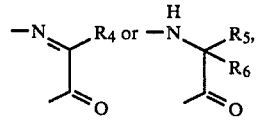

in which R$_4$, R$_5$ and R$_6$ have the same meanings as above, reduction and cyclisation of a compound of the general formula:

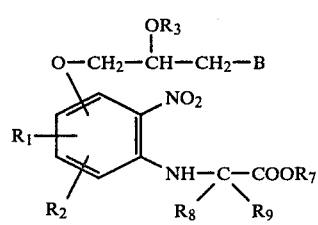 (IX)

in which R$_1$, R$_2$, R$_3$, R$_7$ and B have the same meanings as above and R$_8$ is a hydrogen atom or R$_5$ and R$_9$ is R$_4$ or R$_6$, and, when R$_8$ is a hydrogen atom, subsequent oxidation; or
(g) when A stands for the grouping

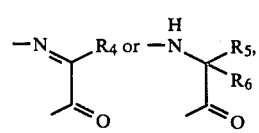

in which R$_4$, R$_5$ and R$_6$ have the same meanings as above, reduction and cyclisation of a compound of the general formula:

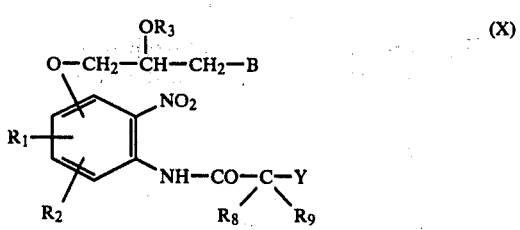

in which $R_1$, $R_2$, $R_3$, $R_8$, $R_9$ and B have the same meanings as above and Y is a reactive group and, when $R_8$ is a hydrogen atom, subsequent oxidation; whereafter, if desired, a compound of general formula (I), in which $R_3$ is a hydrogen atom, is acylated or a substituent in B is, if desired, converted into a different substituent B, protective groups possibly present are removed and the compound obtained of general formula (I) is, if desired, converted into a pharmacologically acceptable salt.

V and Y in compounds of general formulae (II), (V) and (X) stand for all residues which can be nucleophilically substituted, such residues including, for example, halogen atoms, preferably bromine and chlorine atoms, and sulphonic acid ester groups.

The processes according to the present invention are preferably carried out in a solvent which is inert under the reaction conditions, for example, water, ethanol, dioxan or dimethylformamide, optionally in the presence an acid-binding agent. The reactions can also be carried out, after mixing the reaction components, without the use of a solvent. The reactions are carried out by leaving the reaction mixture to stand at ambient temperature or by heating, possibly under an atmosphere of a protective gas.

The reaction of compounds of general formula (IV) with compounds of general formula (V) according to process (b) is preferably carried out with the exclusion of oxygen and in the presence of an acid acceptor. However, it is also possible to use alkali metal salts of the hydroxy compounds of general formula (IV).

The reduction of the group

which is possibly to be carried out can take place by catalytic hydrogenation with a noble metal or nickel catalyst or by means of a complex metal hydride, for example sodium borohydride. Reductions such as are necessary for processes (f) and (g) are preferably carried out with catalytically-activated hydrogen.

Process (f) is preferably carried out under the conditions of hydrogenation; cyclisation can take place with the addition of acid.

The cyclisation according to process (g) takes place with the addition of bases, for example triethylamine or potassium carbonate.

Oxidations which are of importance for processes (e), (f) and (g) are preferably carried out with air, hydrogen peroxide in an alkaline medium or potassium permanganate.

Some of the compounds of general formula (VI) are known (see Federal Republic of Germany Patent Specification No. 27 37 630.3) and those which are not known can be prepared analogously to the processes described therein.

Compounds of general formula (IV) are either known or can be prepared from known phenols analogously to processes (c), (d), (e), (f) or (g).

Compounds of general formula (X) are new and can be obtained from the appropriate 2-nitroanilines by reaction with 2-halocarboxylic acid chlorides.

The subsequent acylation of compounds of general formula (I), in which $OR_3$ is a hydroxyl group, possibly to be carried out can take place in the usual manner by reaction with a reactive acid derivative, for example an acid halide, acid azide or acid anhydride, possibly in the presence of an acid-binding agent, for example pyridine, in a solvent, for example acetone, benzene or dimethylformamide, or also in excess acid.

The subsequent conversion of a substituent in B can be, for example, the conversion of an amino group into an alkylcarbonylamino or alkylsulphonylamido radical. These reactions also take place according to known methods with conventional acylation agents, for example carboxylic acid anhydrides, carboxylic acid chlorides or alkylsulphonic acid chlorides.

As protective groups which may possibly be necessary, there can, in principle, be used all protective groups employed for the intermediate protection of amino or hydroxyl groups which can easily be split off again. The benzyl radical is preferred which, after the reaction according to one of the described processes, can be split off hydrogenolytically in known manner.

The compounds of general formula (I) according to the present invention can be obtained in the form of a racemic mixture. The separation of the racemate into the optically-active forms can be carried out by known methods via the diastereomeric salts with active acids, for example tartaric acid, malic acid or camphor-sulphonic acid.

Under the reaction conditions of the described processes, the new compounds of general formula (I) are preponderantly obtained as acid-addition salts, for example as hydrochlorides, and can be readily converted into the free bases according to known methods.

For the conversion of the compounds of general formula (I) into their pharmacologically acceptable salts, they are reacted, preferably in an organic solvent, with an equivalent amount of an inorganic or organic acid, for example hydrochloric acid, hydrobromic acid, phosphoric acid, sulphuric acid, acetic acid, citric acid or maleic acid.

The present invention also provides pharmaceutical compositions containing at least one of the new compounds in admixture with a solid or liquid pharmaceutical diluent or carrier.

For the preparation of pharmaceutical compositions, the compounds (I) are mixed in known manner with suitable pharmaceutical carrier substances, aroma, flavouring and colouring materials and formed, for example, into tablets or dragees or, with the addition of appropriate adjuvants, suspended or dissolved in water or in an oil, for example olive oil.

The new compounds (I) according to the present invention and the salts thereof can be administered enterally or parenterally in liquid or solid form. As injection medium, it is preferred to use water which can contain the usual additives for injection solutions, such as stabilising agents, solubilising agents or buffers. Additives of this kind include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage can depend upon various factors, such as the manner of administration, species, age and/or individual state of the recipient. In the case of oral administration, the daily dosage to be administered is between about 5 mg. and about 50 mg. for warm-blooded animals with a body weight of about 70 kg.

Apart from the compounds mentioned in the specific Examples, the following compounds are also preferred according to the present invention:

5-{2-hydroxy-3-[2-(2-methoxyphenoxy)-ethylamino]-propoxy}-3,5,6-trimethyl-2-quinoxalinone, 5-[2-hydroxy-3-(3,4-dimethoxyphenethylamino)-propoxy]-3-methyl-5,6-cyclopenteno-2-quinoxalinone, 5-{2-hydroxy-3-[4-(2-methoxyphenoxymethyl)-piperidino]-propoxy}-3-methyl-2-quinoxalinone, 5-{2-hydroxy-3-[4-(2-methoxy-4-methylphenoxymethyl)-piperidino]-propoxy}-3-methyl-2-quinoxalinone, 5-{2-hydroxy-3-[2-(2-methoxyphenoxy)-ethylamino]-propoxy}-2-quinoxalinone, 5-{2-hydroxy-3-[2-(2-methoxyphenoxy)-ethylamino]-propoxy}-3-hydroxymethyl-2-quinoxalinone, 3,4-dihydro-3,3-dimethyl-5-{2-hydroxy-3-[2-(2-methoxyphenoxy)-ethylamino]-propoxy}-2-quinoxalinone, 5-{2-hydroxy-3-[2-(2-methoxyphenoxy)-propylamino]-propoxy}-3-methyl-2-quinoxalinone, 5-{2-hydroxy-3-[2-(2-hydroxyphenoxy)-propylamino]-propoxy}-3-methyl-2-quinoxalinone, 5-[2-hydroxy-3-(2-phenoxyethylamino)-propoxy]-3-methyl-2-quinoxalinone, 5-{2-hydroxy-3-[2-(4-hydroxy-2-methylphenoxy)-ethylamino]-propoxy}-3-methyl-2-quinoxalinone, 5-{2-hydroxy-3-[2-(2-allyloxyphenoxy)-ethylamino]-propoxy}-3-methyl-2-quinoxalinone, 5-{2-hydroxy-3-[2-(2-isopropoxyphenoxy)-ethylamino]-propoxy}-3-methyl-2-quinoxalinone, 5-{2-hydroxy-3-[2-(2-phenoxyphenoxy)-ethylamino]-propoxy}-3-methyl-2-quinoxalinone, 5-{2-hydroxy-3-[2-(2,6-dimethoxyphenoxy)-ethylamino]-propoxy}-3-methyl-2-quinoxalinone, 5-{2-hydroxy-3-[2-(2-alkylphenoxy)-ethylamino]-propoxy}-3-methyl-2-quinoxalinone, 5-{2-hydroxy-3-[2-(2-trifluoromethylphenoxy)-ethylamino]-propoxy}-3-methyl-2-quinoxalinone, 5-{2-hydroxy-3-[2-(2-acetamidophenoxy)-ethylamino]-propoxy}-3-methyl-2-quinoxalinone, 5-{2-hydroxy-3-[2-(2-methylthiophenoxy)-ethylamino]-propoxy}-3-methyl-2-quinoxalinone, and 5-{2-hydroxy-3-[2-(2-phenoxyphenethylamino)-ethylamino]-propoxy}-3-methyl-2-quinoxalinone.

The following Examples are given for the purpose of illustrating the present invention:

EXAMPLE 1

8-(3-tert.-Butylamino-2-hydroxypropoxy)-1,4H-cyclobuteno[1,2-b]quinoxaline-3',4'-dione hydrochloride 10.8 g. 2,3-diamino-1-(2-hydroxy-3-tert.-butylaminopropoxy)-benzene trihydrochloride, 3.4 g. 3,4-dihydroxy-3-cyclobutene-1,2-dione and 25 ml. 4 N hydrochloric acid are heated under reflux for 10 minutes, then allowed to cool and the crystals which precipitate out are isolated. These are recrystallised from methanol/water, with the addition of active charcoal, to give 4.55 g. (42% of theory) 8-(3-tert.-butylamino-2-hydroxypropoxy)-1,4H-cyclobuteno[1,2-b]quinoxaline-3',4'-dione hydrochloride.

The following compounds are obtained in an analogous manner from 3,4-dihydroxy-3-cyclobutene-1,2-dione:

| | designation | yield % of theory | m.p. °C. (solvent) |
|---|---|---|---|
| (a) | 8-[2-hydroxy-3-(3,4-dimethoxyphenethylamino)-propoxy]-1,4H-cyclobuteno[1,2-b]quinoxaline-3',4'-dione hydrochloride from 2,3-diamino-1-[2-hydroxy-3-(3,4-dimethoxyphenethylamino)-propoxy]-benzene trihydrochloride | 31 | 214–216 (methanol) |
| (b) | 8-[2-hydroxy-3-(4-phenoxymethyl-piperidino)-propoxy]-1,4H-cyclobuteno[1,2-b]quinoxaline-3',4'-dione hydrochloride from 2,3-diamino-1-[2-hydroxy-3-(4-phenoxymethylpiperidino)-propoxy]-benzene trihydrochloride | 26 | 243–245 (ethanol/water) |
| (c) | 8-[2-hydroxy-3-(3,4-dimethoxyphenethylamino)-propoxy]-5-methyl-1,4H-cyclobuteno[1,2-b]-quinoxaline-3',4'-dione hydrochloride from 2,3-diamino-4-methyl-1-[2-hydroxy-3-(3,4-dimethoxyphenethylamino)-propoxy]-benzene trihydrochloride | 31 | 240–242 (ethanol) |
| (d) | 8-{2-hydroxy-3-[2-(2-hydroxyphenoxy)-ethylamino]-propoxy}-1,4H-cyclobuteno[1,2-b]-quinoxaline-3',4'-dione hydrochloride from 2,3-diamino-1-{2-hydroxy-3-[2-(2-hydroxyphenoxy)-ethylamino]-propoxy}-benzene trihydrochloride | 23 | 262–264 (water) |
| (e) | 8-{2-hydroxy-3-[2-(2-phenoxy)-ethylamino]-propoxy}-5-methyl-1,4H-cyclobuteno-[1,2-b]quinoxaline-3',4'-dione hydrochloride from 2,3-diamino-4-methyl-1-{2-hydroxy-3-[2-(2-hydroxyphenoxy)-ethylamino]-propoxy}-benzene trihydrochloride | 15 | 268–270 (ethanol/water) |
| (f) | 8-{2-hydroxy-3-[2-(2-methoxyphenoxy)-ethylamino]-propoxy}-5-methyl-1,4H-cyclobuteno-[1,2-b]quinoxaline-3',4'-dione hydrochloride from 2,3-diamino-4-methyl-1-{2-hydroxy-3-[2-(2-methoxyphenoxy)-ethylamino]-propoxy}-benzene trihydrochloride | 38 | 207–210 (ethanol/water) |
| (g) | 8-(2-hydroxy-3-(S)-2-butylamino- | 16 | 325–327 |

-continued

| | designation | yield % of theory | m.p. °C. (solvent) |
|---|---|---|---|
| | propoxy)-1,4H-cyclobuteno-[1,2-b]quinoxaline-3',4'-dione hydrochloride from 2,3-diamino-1-(2-hydroxy-3-(S)-2-butylaminopropoxy)-benzene trihydrochloride | | (ethanol/ water) |
| (h) | 8-(2-hydroxy-3-(R)-2-butylaminopropoxy)-1,4H-cyclobuteno-[1,2-b]quinoxaline-3',4'-dione hydrochloride from 2,3-diamino-1-(2-hydroxy-3-(R)-2-butylaminopropoxy)-benzene trihydrochloride | 20 | 257–260 (ethanol/ water) |
| (i) | 8-{2-hydroxy-3-[2-(2-methoxyphenoxy)-propylamino]-propoxy}-1,4H-cyclobuteno[1,2-b]quinoxaline-3',4'-dione hydrochloride from 2,3-diamino-4-methyl-1-{2-hydroxy-3-[2-(2-methoxyphenoxy)-propylamino]-propoxy}-benzene trihydrochloride | 28 | 162–165 (isopropanol) |
| (k) | 8-{2-hydroxy-3-[2-(2-methylphenoxy)-ethylamino]-propoxy}-1,4H-cyclobuteno[1,2-b]-quinoxaline-3',4'-dione hydrochloride from 2,3-diamino-1-{2-hydroxy-3-[2-(2-methylphenoxy)-ethylamino]-propoxy}-benzene trihydrochloride | 69 | 204–207 (dioxan/ water) |

EXAMPLE 2

5-(2-Hydroxy-3-tert.-butylaminopropoxy)-3-methyl-2-quinoxalinone hydrochloride and 8-(2-Hydroxy-3-tert.-butylaminopropoxy)-3-methyl-2-quinoxalinone hydrochloride 7.2 g. 2,3-Diamino-1-(2-hydroxy-3-tert.-butylaminopropoxy)-benzene trihydrochloride are dissolved, with heating, in 40 ml. water. 2.28 g. Acetylenedicarboxylic acid, dissolved in 20 ml. water, are added to the hot solution. After 20 hours, the reaction mixture is evaporated to dryness in a vacuum and the evaporation residue is fractionally crystallised from ethanol. The first crystallisate of 3.1 g. melts, after recrystallisation from ethanol with the addition of active charcoal, at 274°–275° C. This compound is 5-(2-hydroxy-3-tert.-butylamino-propoxy)-3-methyl-2-quinoxalinone hydrochloride. 0.83 g. of a second crystallisate are obtained with a melting point of 225°–228° C. This is 8-(2-hydroxy-3-tert.-butylamino-propoxy)-3-methyl-2-quinoxalinone hydrochloride.

The following compounds are obtained in an analogous manner from substituted o-phenylenediamines and acetylenedicarboxylic acid:

| | designation | m.p. °C. (solvent) |
|---|---|---|
| a(1) | 5-[2-hydroxy-3-(3,4-dimethoxyphenethylamino)-propoxy]-3-methyl-2-quinoxalinone and | 163–164 (ethanol) |
| a(2) | 8-[2-hydroxy-3-(3,4-dimethoxyphenethylamino)-propoxy]-3-methyl-2-quinoxalinone hydrochloride from 2,3-diamino-1-[2-hydroxy-3-(3,4-dimethoxyphenethylamino)-propoxy]-benzene trihydrochloride | 229–231 (ethanol) |
| b(1) | 5-[2-hydroxy-3-(3,4-dimethoxyphenethylamino)-propoxy]-3,8-dimethyl-2-quinoxalinone hydrochloride and | 218–220 (ethanol/ methanol) |
| b(2) | 8-[2-hydroxy-3-(3,4-dimethoxyphenethylamino)-propoxy]-3,5-dimethyl-2-quinoxalinone hydrochloride (purification over a silica gel column with chloroform/methanol 8:2 (v/v) as elution agent) from 2,3-diamino-[2-hydroxy-3-(3,4-dimethoxyphenethylamino)-propoxy]-4-methyl-benzene trihydrochloride | 228–230 (ethanol/ isopropanol) |
| c(1) | 5-{2-hydroxy-3-[2-(2-hydroxyphenoxy)-ethylamino]-propoxy}-3,8-dimethyl-2-quinoxalinone hydrochloride and | 263–265 (ethanol/ methanol) |
| c(2) | 8-{2-hydroxy-3-[2-(2-hydroxyphenoxy)-ethylamino]-propoxy}-3,5-dimethyl-2-quinoxalinone hydrochloride from 2,3-diamino-{2-hydroxy-3-[2-(2-hydroxyphenoxy)-ethylamino]-propoxy}-4-methyl-benzene trihydrochloride | 272–273 (ethanol/ methanol) |
| d(1) | 5-{2-hydroxy-3-[4-(2-pyridyloxymethyl)-piperidino]-propoxy}-3-methyl-2-quinoxalinone hydrochloride and | 194–196 (ethanol) |
| d(2) | 8-{2-hydroxy-3-[4-(2-pyridyloxymethyl)-piperidino]-propoxy}-3-methyl-2-quinoxalinone (purification over a silica gel column with chloroform/methanol 8:2 (v/v) as elution agent) from 2,3-diamino-1-{2-hydroxy-3-[4-(2-pyridyloxymethyl)-piperidino]-propoxy}-benzene trihydrochloride | 190–192 (methanol) |
| e(1) | 5-[2-hydroxy-3-(4-phenoxymethyl-piperidino)-propoxy]-3-methyl-2-quinoxalinone and | 174–177 (methanol) |
| e(2) | 8-[2-hydroxy-3-(4-phenoxymethyl-piperidino)-propoxy]-3-methyl-2-quinoxalinone from 2,3-diamino-1-[2-hydroxy-3-(4-phenoxymethylpiperidino)-propoxy]-benzene trihydrochloride | 207–209 (methanol) |
| f(1) | 5-{2-hydroxy-3-[2-(2-hydroxyphenoxy)-ethylamino]-propoxy}-3-methyl-2-quinoxalinone and | 193–194 (ethanol) |
| f(2) | 8-{2-hydroxy-3-[2-(2-hydroxyphenoxy)-ethylamino]-propoxy}-3-methyl-2-quinoxalinone hydrochloride from 2,3-diamino-{2-hydroxy-3-[2-(2-hydroxyphenoxy)-ethylamino]-propoxy}-benzene trihydrochloride | 238–240 (methanol) |
| g(1) | 5-{2-hydroxy-3-[2-(2-methoxyphenoxy)-ethylamino]-propoxy}-3-methyl-2-quinoxalinone hydrochloride and | 197–199 (methanol) |
| g(2) | 8-{2-hydroxy-3-[2-(2-methoxyphenoxy)-ethylamino]-propoxy}-3-methyl-2-quinoxalinone hydrochloride from 2,3-diamino-1-{2-hydroxy-3-[2-(2-methoxyphenoxy)-ethylamino]-propoxy}-benzene trihydrochloride | 253–254 (methanol) |
| h(1) | 5-(2-hydroxy-3-(S)-2-butylaminopropoxy)-3-methyl-2-quinoxalinone hydrochloride and | 256–258 (ethanol/ diethyl ether) |
| h(2) | 8-(2-hydroxy-3-(S)-2-butylaminopropoxy)-3-methyl-2-quinoxalinone hydrochloride from 2,3-diamino-1-(2-hydroxy-3-(S)-2-butylaminopropoxy)-benzene trihydrochloride (separation via a silica gel column with chloroform/methanol 8:2 (v/v) as elution agent) | 190–193 (ethanol/ diethyl ether) |
| i(1) | 5-(2-hydroxy-3-(R)-2-butylaminopropoxy)-3-methyl-2-quinoxalinone | 255–257 (ethanol/ |

-continued

| designation | m.p. °C. (solvent) |
|---|---|
| hydrochloride and | diethyl ether) |
| i(2) 8-(2-hydroxy-3-(R)-2-butylamino-propoxy)-3-methyl-2-quinoxalinone hydrochloride from 2,3-diamino-1-(2-hydroxy-3-(R)-2-butylaminopropoxy)-benzene trihydrochloride (separation via a silica gel column with chloroform/methanol 8:2 (v/v) as elution agent) | 191–194 (ethanol/ diethyl ether) |
| k(1) 5-{2-hydroxy-3-[4-(4-(2)-benzimidazol-inonyloxymethyl)-piperidino]-propoxy}-3-methyl-2-quinoxalinone and | 253–254 (methanol) |
| k(2) 8-{2-hydroxy-3-[4-(4-(2)-benzimidazol-inonyloxymethyl)-piperidino]-propoxy}-3-methyl-2-quinoxalinone from 2,3-diamino-1-{2-hydroxy-3-[4-(4-(2)-benzimidazolinonyloxymethyl)-piperidino]-propoxy}-benzene trihydrochloride | |
| l(1) 5-[2-hydroxy-3-(2-phenoxyethylamino)-propoxy]-3,7-dimethyl-2-quinoxalinone hydrochloride and | 226–229 (ethanol/ methanol) |
| l(2) 8-[2-hydroxy-3-(2-phenoxyethylamino)-propoxy]-3,6-dimethyl-2-dquinoxalinone hydrochloride from 2,3-diamino-1-[2-hydroxy-3-(2-phenoxy-ethylamino)-propoxy]-5-methyl-benzene trihydrochloride | |

EXAMPLE 3

5-[2-Hydroxy-3-(3,4-dimethoxyphenethylamino)-propoxy]-3,8-dimethyl-2-quinoxalinone hydrochloride 28.0 g. 2,3-Dinitro-1-[2-hydroxy-3-(N-benzyl-3,4-dimethoxyphenethylamino)-propoxy]-4-methylbenzene are boiled under reflux with 15.9 g. alanine, 15.0 g. sodium bicarbonate and 250 ml. ethylene glycol monomethyl ether for 4 hours. The reaction mixture is poured into 600 ml. water and then extracted six times with 100 ml. amounts of chloroform. The combined chloroform extracts are dried over anhydrous sodium sulphate. After completely evaporating in a vacuum, there are obtained 32.0 g. of an oily residue which is taken up in 280 ml. ethanol and mixed with 4 ml. concentrated sulphuric acid. After boiling under reflux for 4 hours, the reaction mixture is distilled off to dryness, the residue is taken up in 300 ml. chloroform, washed with water, 10% aqueous sodium bicarbonate solution and again with water and, after drying over anhydrous sodium sulphate and clarifying with active charcoal, evaporated to give 33.5 g. oily ethyl 2-{6-[2-hydroxy-3-(N-benzyl-3,4-dimethoxyphenethylamino)-propoxy]-3-methyl-2-nitroanilino}-propionate.

33.0 g. Ethyl 2-{6-[2-hydroxy-3-(N-benzyl-3,4-dimethoxyphenethylamino)-propoxy]-3-methyl-2-nitroanilino}-propionate are hydrogenated in 400 ml. ethanol over 3.5 g. platinum dioxide and subsequently over 8.0 g. 10% palladium-charcoal at normal pressure and 50° C. The catalyst is removed and the reaction mixture is acidified with 2 N hydrochloric acid and then stirred vigorously for 1 hour with the addition of active charcoal. The reaction mixture is filtered and the filtrate concentrated to 200 ml. The precipitated crystals (7.0 g., corresponding to 25% of theory, referred to the amount of dinitro compound used) are identical (thin layer chromatogram and mixed melting point) with the compound obtained in Example (2b) (1).

EXAMPLE 4

5-{2-Hydroxy-3-[2-(2-methoxyphenoxy)-ethylamino]-propoxy}-3-methyl-2-quinoxalinone hydrochloride 52.3 g. 2,3-Dinitro-1-{2-hydroxy-3-[N-benzyl-2-(2-methoxyphenoxy)-ethylamino]-propoxy}-benzene, 26.7 g. alanine, 25.2 g. sodium bicarbonate, 400 ml. ethanol and 200 ml. water are boiled under reflux for 5 hours. The reaction mixture is then completely evaporated, dissolved in 800 ml. water and 300 ml. ethylene glycol monomethyl ether and extracted with a total of 1500 ml. dichloromethane. The organic phase is dried over anhydrous sodium sulphate and evaporated to give 56.2 g. (100% of theory) sodium 2-{6-{2-hydroxy-3-[N-benzyl-2-(2-methoxyphenoxy)-ethylamino]-propoxy}-2-nitroanilino}-propionate.

31.2 g. of this sodium salt are hydrogenated in 450 ml. ethanol and 50 ml. water at 50° C. and 5 bar pressure over 6 g. Raney nickel. After filtration and adjustment of the filtrate to pH 4 with 2 N hydrochloric acid, the protective group is removed by hydrogenation over 8 g. 5% palladium-charcoal at 60° C. and normal pressure. The reaction mixture is evaporated to dryness and the residue is taken up in 250 ml. ethanol, freed from precipitated salt and air is passed through the solution. After standing for 10 hours, the precipitated crystals are filtered off with suction. There are obtained 5.65 g. (23% of theory) of product which, after again recrystallising from ethanol, is identical with the product of Example (2g) (1).

EXAMPLE 5

5-{2-Hydroxy-[2-(2-methoxyphenoxy)-ethylamino]-propoxy}-3-(2)-propyl-2-quinoxalinone hydrochloride Analogously to Example 4, from 1-{2-hydroxy-[N-benzyl-2-(2-methoxyphenoxy)-ethylamino]-propoxy}-2,3-dinitrobenzene and valine, there is obtained 5-{2-hydroxy-[2-(2-methoxyphenoxy)-ethylamino]-propoxy}-3-(2)-propyl-2-quinoxalinone hydrochloride which, after recrystallising from ethanol, has a melting point of 174°–176° C.

EXAMPLE 6

Tablets containing active material

| | | for 1 tablet | for 100,000 tablets |
|---|---|---|---|
| I. | active materials [5-{2-hydroxy-3-[2-(2-methoxy-phenoxy)-ethylamino]-propoxy}-3-methyl-2-quinoxalinone hydrochloride] | 10.000 mg. | 1.000 kg. |
| | lactose | 67.000 mg. | 6.700 kg. |
| | maize starch | 35.000 mg. | 4.500 kg. |
| II. | polyvinylpyrrolidone (M.W. 30,000) | 3.000 mg. | 0.300 kg. |
| III. | sodium carboxymethyl-amylopectin | 4.000 mg. | 0.400 kg. |
| | cellulose powder | 20.000 mg. | 2.000 kg. |
| | magnesium stearate | 1.000 mg. | 0.100 kg. |
| | | 140.000 mg. | 14.000 kg. |
| | water for granulation | | 1.000 kg. |

Production: Substances I are granulated with an aqueous solution of II, dried and sieved. The granulate is mixed with the substances III to give a tabletting mass.

Tabletting is carried out to give tablets of 7 mm. diameter and 140 mg. weight.

The effectiveness of the compounds of the invention as vaso-dilators and beta-receptor blocking agents are illustrated by the following tests in combination.

1. Beta Receptor Blocking Activity Experiments

The heart beat frequency of rabbits was monitored via implanted electrode and recorded on a frequency counter having a measurement time of 15 seconds. Isoprenalin was then injected intravenously via an ear vein, initially at 1 µg/kg inducing an increase in heart beat frequency of from ca. 210 beats/min. to 350 beats/min. Subsequently, the test compounds were administered in increased dosage (1+1+2+4+8 units with an initial dosage of 125 µg/kg) intravenously and the heart frequency increase after isoprenalin treatment again recorded. The inhibition of isoprenalin tachycardia was taken as a measure of the beta-blockage activity of the test compounds. The dosage which reduced the isoprenalin increase by 30 or 50% ($HD_{30}$ or $HD_{50}$) was determined for each test substance.

2. Vaso Dilator Experiments

Rabbits were anesthesized with urethane and a catheter implanted in the middle ear artery (A. femoralis) for a continuous measurement of their arterial blood pressure. The blood pressure measurements were effected using an electromechanical transducer (Statham P 23 Dd) and were recorded in a direct printer and utilized after calibration with a mercury manometer.

After determination of the starting value both jugular arteries (A. carotis) were occluded for two minutes and blood pressure thereby temporarily increased (CSE-reflex). The test compound was then injected at the lowest experimental dosage (125 µg/kg as in Experiment 1) intravenously and eight minutes later the CSE-reflex was again induced.

Test compounds which under these conditions moderated the CSE-induced blood pressure increase were demonstrated to be vaso-dilators and the dosage which decreased the CSE-reflex by 30 mm Hg was determined (designed as $DE_{-30}$ mm Hg in the table below).

The results from the above experiments 1 and 2 are set forth in the table below. Propranolol was included as a companion substance and a "relative potency" figure (RP) is included below to compare the efficacy of the test compounds to propranolol which was assigned an RP of 1.

All of the test substances reported below are strong beta-blockers and additionally exhibit pronounced blood pressure depressant properties. Since both effects are desired, it is advantageous to find both effects as dosages which are as close together as possible since otherwise the efficacy of one or the other effect would be reduced because of under-dosing.

Vaso-Dilating and Beta-blocking Activity of Inventive Compounds In Comparison to Propanolol*

| Example No. | $HD_{30}\,f_{cor}$ µg/kg i.v. | $HD_{50}\,f_{cor}$ µg/kg i.v. | RP | $DE_{-30}$ µg/kg i.v. |
|---|---|---|---|---|
| Propranolol | 92 | 393 | 1 | >3550 |
| 2.1 | 3.6 | 12.3 | 30 | — |
| 2.2 | 4.4 | 18.4 | 22 | — |
| 1 | 321 | 868 | 0.45 | — |
| 1a | 594 | 3282 | 0.1 | — |
| 2a.1 | 156 | 588 | 0.66 | 14900 |
| 2b.1 | 400 | 1091 | 0.36 | 7900 |
| 2c.1 | 52 | 212 | 1.85 | 1240 |
| 2e.1 | 152 | 472 | 0.8 | — |
| 2f.1 | 38 | 180 | 2.2 | 1940 |
| 2g.1 | 173 | 669 | 0.6 | 513 |
| 1h | 331 | 873 | 0.45 | — |
| 1g | 338 | 718 | 0.54 | — |
| 2h | 31 | 132 | 2.9 | 6880 |
| 2i | 25 | 83 | 4.7 | 11890 |

The results indicate that the inventive compounds exhibit substantially greater beta-blocking activity then the prior art material.

In actual administration of the invention compounds, e.g., in the treatment of hypertension or angina pectoris, the appropriate dosage is of course dependent on the condition of the patient and the specific infirmity to be treated. In general, treatment should begin with a small doses (e.g., 5,10,20 or 50 mg) and increased gradually depending upon the patient's response. The dosage can be increased at 5 to 7 day intervals until an average daily dosage of 20 to 200 mg is reached. For maintenance, 2 to 4 doses a day are usually required. These dosage levels will generally be appropriate, both for achieving a vaso dilating effect, i.e., for reducing blood pressure, and for inhibition of adrenergic beta-receptor activity.

The present invention provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative, but not limitative of the present invention and that other embodiments within the spirit and scope of the invention will suggest themselves to those skilled in the art.

What is claimed is:

1. An aminopropanol compound of the formula

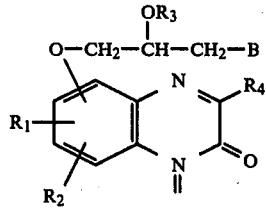

wherein
R₁ and R₂ are individually selected from hydrogen and lower alkyl; or
R₁ and R₂ together represent an alkylene radical of between 2 and 4 carbon atoms;
R₃ is hydrogen or acyl in the form of an acid residue of an hydrocarbon aliphatic carboxylic acid containing 2 to 6 carbon atoms, an aromatic carboxylic acid or of an aromatic carboxylic acid substituted with up to two substituents selected from halogen, lower alkyl or lower alkoxy radicals;

R₄ is hydrogen or lower alkyl optionally including one substituent selected from hydroxyl, halogen or lower alkylthio; and B is alkylamino which optionally carries on the alkyl moiety a phenyl and/or a phenoxy radical optionally substituted by one of halogen, hydroxyl, lower alkyl, lower acyl, lower alkylthio, acylamino, aminocarbonyl, lower alkoxy, lower alkenyloxy, phenoxy, lower alkenyl, lower alkylsulphonyl, lower alkylsulphinyl or haloalkyl; or B is a phenyl-, naphthyl-, pyridyl-, pyrimidyl-, or benzimidazolinyl-oxymethylpiperidine radical, optionally substituted by at least one of halogen, hydroxyl or lower alkyl, hydroxyl alkyl or carboxyamido alkyl, or by lower alkoxy, lower acyl, amino, carboxamido, lower alkanecarboxamido or lower alkylsulphonylamino; wherein the acyl radicals or acyl moieties in either B definition are in the form of an acid residue of an hydrocarbon aliphatic carboxylic acid containing 2 to 6 carbon atoms, an aromatic carboxylic acid or of an aromatic carboxylic acid substituted with up to two substituents selected from halogen, lower alkyl or lower alkoxy radicals, the piperidine radical in each case being fixed to the propanol chain by its nitrogen atom;

and the pharmacologically acceptable salts thereof.

2. A pharmaceutical composition with blood pressure lowering and β-blocking properties comprising a pharmaceutically acceptable carrier and, in effective amount, an aminopropanol compound as claimed in claim 1.

3. A method of treating an afflicted subject for high blood pressure, angina pectoris or circulatory diseases by blood pressure lowering and beta-blocking, which comprises administering to the subject a pharmacologically effective amount of a pharmaceutical composition as claimed in claim 2.

4. Aminopropanol compound as claimed in claim 1 wherein B is phenyloxymethylpiperidine or naphthyloxymethylpiperidine.

5. Aminopropanol compound as claimed in claim 1, wherein R₁ and R₂ are hydrogen.

6. Aminopropanol compound as claimed in claim 1, wherein one of R₁ and R₂ is lower alkyl.

7. Aminopropanol compound as claimed in claim 1, wherein R₁ and R₂ together represent lower alkylene.

8. Aminopropanol compound as claimed in claim 1, wherein R₃ is hydrogen.

9. Aminopropanol compound as claimed in claim 1, wherein R₃ is acyl.

10. Aminopropanol compound as claimed in claim 1, wherein B is alkylamino or substituted alkylamino.

11. Aminopropanol compound as claimed in claim 1 wherein B is pyridyloxymethylpiperidine or benzimidazolinyloxymethylpiperidine.

12. Method as claimed in claim 3, wherein said circulatory cardiac disease is angina pectoris.

13. Aminopropanol compound as claimed in claim 1, designated 5-(2-hydroxy-3-tert.-butylaminopropoxy)-3-methyl-2-quinoxalinone hydrochloride.

14. Aminopropanol compound as claimed in claim 1, designated 8-(2-hydroxy-3-tert.-butylamino-propoxy)-3-methyl-2-quinoxalinone hydrochloride.

15. Aminopropanol compound as claimed in claim 1 designated 5-[2-hydroxy-3-(3,4-dimethoxyphenethylamino)-propoxy]-3,8-dimethyl-2-quinoxalinone hydrochloride.

16. Aminopropanol compound as claimed in claim 1 designated 5-{2-hydroxy-3-[2-(2-hydroxyphenoxy)-ethylamino]-propoxy}-3,8-dimethyl-2-quinoxalinone hydrochloride.

17. Aminopropanol compound as claimed in claim 1, designated 5-{2-hydroxy-3-[2-(2-methoxyphenoxy)-ethylamino]-propoxy}-3-methyl-2-quinoxalinone hydrochloride.

18. Method as claimed in claim 3, wherein said circulatory and cardiac disease is hypertension.

19. A composition as claimed in claim 2 wherein said compound is selected from 5-(2-hydroxy-3-tert.-butylaminopropoxy)-3-methyl-2-quinoxalinone hydrochloride;

8-(2-hydroxy-3-tert.-butylaminopropoxy)-3-methyl-2-quinoxalinone hydrochloride;

5-[2-hydroxy-3-(3,4-dimethoxyphenethyl-amino)-propoxy]-3,8-dimethyl-2-quinoxalinone hydrochloride;

5-{2-hydroxy-3-[2-(2-hydroxyphenoxy)-ethylamino]-propoxy}-3,8-dimethyl-2-quinoxalinone hydrochlorides; and 5-{2-hydroxy-3-[2-(2-methoxyphenoxy)-ethylamino]-propoxy}-3-methyl-2-quinoxalinone hydrochloride.

20. Method as claimed in claim 3, wherein such compound is applied in a prophylactic manner.

21. A method as claimed in claim 3, wherein said pharmaceutical composition contains:

5-(2-hydroxy-3-tert.-butylaminopropoxy)-3-methyl-2-quinoxalinone hydrochloride;

8-(2-hydroxy-3-tert.-butylaminopropoxy)-3-methyl-2-quinoxalinone hydrochloride;

5-{2-hydroxy-3-(3,4-dimethoxyphenethyl-amino)-propoxy}-3,8-dimethyl-2-quinoxalinone hydrochloride;

5-{2-hydroxy-3-{2-(2-hydroxyphenoxy)-ethylamino}-propoxy}-3,8-dimethyl-2-quinoxalinone hydrochloride; or 5-{2-hydroxy-3-{2-(2-methoxyphenoxy)-ethylamino}-propoxy}-3-methyl-2-quinoxalinone hydrochloride.

* * * * *

UNITED STATES PATENT AND TRADEMARK OFFICE
CERTIFICATE OF CORRECTION

PATENT NO. : 4,438,116
DATED : March 20, 1984
INVENTOR(S) : Carl H. Ross et al

It is certified that error appears in the above-identified patent and that said Letters Patent is hereby corrected as shown below:

Col. 14, in formula of claim 1, at the lower "N",

" H " should be -- H --.

Signed and Sealed this

Sixteenth Day of April 1985

[SEAL]

Attest:

DONALD J. QUIGG

Attesting Officer

Acting Commissioner of Patents and Trademarks